United States Patent [19]

Pallarito

[11] Patent Number: 5,733,277
[45] Date of Patent: Mar. 31, 1998

[54] OPTICAL FIBRE AND LASER FOR REMOVAL OF ARTERIAL OR VASCULAR OBSTRUCTIONS

[76] Inventor: Allan L. Pallarito, 13750 Omega Cir., Littleton, Colo. 80124

[21] Appl. No.: 425,247

[22] Filed: Apr. 17, 1995

Related U.S. Application Data

[63] Continuation of Ser. No. 264,005, Jun. 22, 1994, abandoned.

[51] Int. Cl.[6] ................................. A61B 17/36
[52] U.S. Cl. ...................... 606/7; 606/15; 606/16
[58] Field of Search .................... 606/7, 13, 1, 17, 606/10; 607/88, 89

[56] References Cited

U.S. PATENT DOCUMENTS

| | | |
|---|---|---|
| 3,858,577 | 1/1975 | Bass et al. . |
| 4,072,147 | 2/1978 | Hett . |
| 4,146,019 | 3/1979 | Bass et al. . |
| 4,207,874 | 6/1980 | Choy . |
| 4,445,892 | 5/1984 | Hussein et al. . |
| 4,794,931 | 1/1989 | Yock .................... 128/660.3 X |
| 4,819,630 | 4/1989 | DeHart ....................... 606/15 |
| 4,862,887 | 9/1989 | Weber et al. ................. 606/7 X |
| 4,929,246 | 5/1990 | Sinofsky . |
| 4,976,710 | 12/1990 | Mackin . |
| 5,009,655 | 4/1991 | Daignault, Jr. et al. . |
| 5,029,588 | 7/1991 | Yock et al. ................. 606/7 X |
| 5,034,010 | 7/1991 | Kittrell et al. . |
| 5,061,265 | 10/1991 | Abela et al. ................. 606/7 |
| 5,104,392 | 4/1992 | Kittrell et al. . |
| 5,106,387 | 4/1992 | Kittrell et al. . |
| 5,125,925 | 6/1992 | Lundahl ...................... 606/15 |
| 5,140,987 | 8/1992 | Schuger et al. . |
| 5,176,675 | 1/1993 | Watson et al. . |
| 5,184,602 | 2/1993 | Anapliotis et al. ............. 128/6 |
| 5,188,634 | 2/1993 | Hussein et al. ............... 606/15 |
| 5,207,672 | 5/1993 | Roth et al. .................. 606/7 X |
| 5,210,814 | 5/1993 | McNally .................... 128/6 X |
| 5,222,953 | 6/1993 | Dowlatshahi ................ 606/15 |
| 5,292,320 | 3/1994 | Brown et al. . |
| 5,409,483 | 4/1995 | Campbell et al. ............ 606/15 |
| 5,415,654 | 5/1995 | Daikuzono .................. 606/15 |
| 5,456,681 | 10/1995 | Hajjar ........................ 606/15 |
| 5,464,404 | 11/1995 | Abela et al. ................. 606/15 |

OTHER PUBLICATIONS

New Focus, Inc., "Tunable Lasers".
New Focus, Inc. "the Picomotor".
Thorlabs Inc., Jan. 1994 Catalog.
Focal Technologies Inc., Data Sheets on Fiber Optic Rotary Joint, Model Nos. 190, 197 and 145.
BEI Motion Systems Co., "Motion Control Components and Systems".

*Primary Examiner*—Angela D. Sykes
*Assistant Examiner*—Michael Peffley
*Attorney, Agent, or Firm*—Jenkens & Gilchrist, P.C.

[57] ABSTRACT

An apparatus and method of ablating obstructing vascular or arterial material is provided including a pre-polished optical fiber for providing a specific laser light path focal point inserted within a catheter having a protective shield. The optical fiber may be controlled for axial and rotational movement via an optical rotary coupler and a rotary axial stepper to provide rotation speed of up to 5,000 rpm and incremental axial movement from between 1 micron to 1 millimeter. A laser light source is provided for adjustment of the wavelength of the laser light emitted from the end face of the optical fiber to correspond to the absorption characteristics of the material to be ablated.

15 Claims, 1 Drawing Sheet

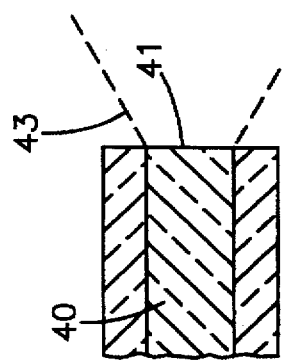
FLAT POLISH FIG.1
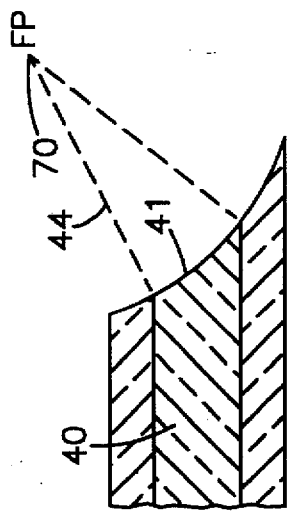
ANGLE POLISH FIG.2
ANGLE CONCAVE POLISH FIG.3
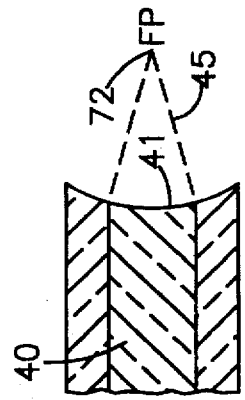
END CONCAVE POLISH FIG.4
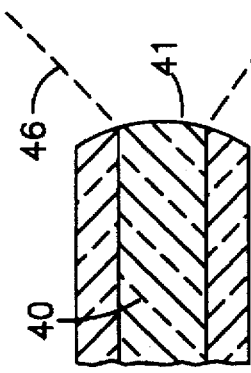
END CONVEX POLISH FIG.5
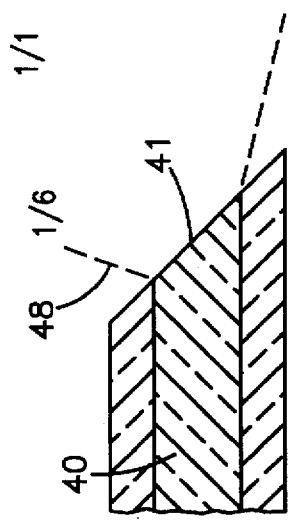
ANGLE CONVEX POLISH FIG.6
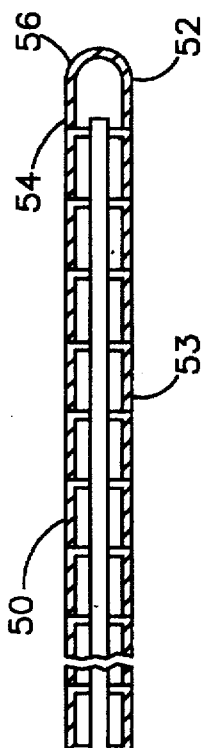
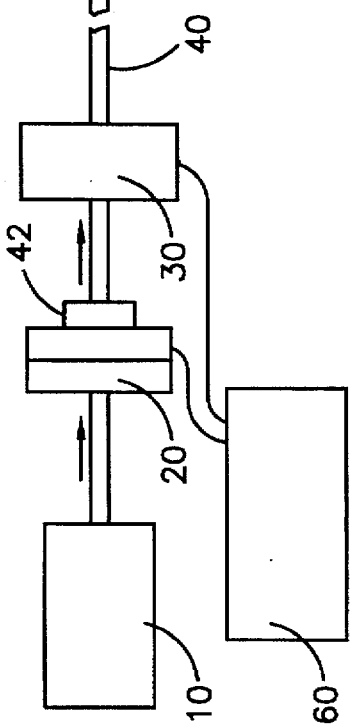
FIG.7

5,733,277

OPTICAL FIBRE AND LASER FOR REMOVAL OF ARTERIAL OR VASCULAR OBSTRUCTIONS

This is a continuation of application Ser. No. 08/264,005, filed on Jun. 22, 1994, which was abandoned upon the filing hereof.

BACKGROUND OF THE INVENTION

This invention relates to devices in which an optical fiber, via a micro lens, delivers laser radiation for medical applications such as the removal of arterial or vascular obstructions.

Fiber optic laser catheters have been developed that use flexible or rigid hollow tubular devices containing optical fibers are inserted into veins or arteries to illuminate internal parts of the body for diagnostic purposes. This is the attention of the device described in U.S. Pat. No. 4,207,874 issued to D. S. J. Choy on Jun. 17, 1980. The sole described use for the removal of thrombus in veins for applications in the circulatory system. The Choy device relies on viewing the obstruction in the vein via the viewing bundle. In the case of coronary arteries the Choy device does not include the advantages of rotary application of laser light, or lateral movement.

M. Bass, in U.S. Pat. Nos. 3,858,577 and 4,146,019 uses a flexible fiber optic endoscope or viewing a body cavity. The endoscope of Bass does not inlude the advantage of having the optical fiber contained within the windowed enclosure, the field of view in from of the endoscope must be purged of all non-transparent fluids and is therefore not intended for use in the vascular system.

J. H. Hett in U.S. Pat. No. 4,072,147 describes a device for viewing and for carrying laser radiation into a body cavity. This endoscope device contains a fiber optic bundle image transmitter connected to an eyepiece for viewing; a spotter light path which indicates where the endoscope is aimed; and optical fibers to deliver therapeutic radiation to that visualized spot. This instrument utilizes a protective transparent cover over the distal end of the instrument. The Hett instrument is designed for direct visualization by eye. The spotter beam, and therapeutic radiation, is delivered to a single location. In a blood vessel, treatment would be limited to one spot at a time. In the case of coronary arteries the advantage of rotary application of laser light, or computer controlled positioning is not provided by the Hett patent.

Hussein, et al, in U.S. Pat. No. 4,445,892, describes a vascular fiber optic catheter with two inflatable balloons which can seal off a segment of a blood vessel allowing it to be purged. Therapeutic laser radiation is delivered at an angle, however Hussein also does not provide the advantage of rotational laser light delivery, or computer controlled positioning.

In Kittrel et al. U.S. Pat. No. 5,104,392, a multi fiber laser catheter is described that provides controlled delivery of laser light via a computer controlled fiber selection shutter. A transparent protective shield is provided at the distal end of the catheter for displacing intravascular blood. A fiber is selected based upon the plaque target to be removed. However, Kittrel nor any of the above references provide the advantage of complete axial, lateral, circumferential and rotational movement to allow for precise ablation of vascular or arterial obstructions.

Accordingly, it is an object of the present invention to provide an optical fiber and laser apparatus which provides for precision movement of an optical fiber for ablation in three axis of motion.

SUMMARY OF THE INVENTION

The present invention provides for an optical fiber and laser apparatus for removal of arterial and vascular obstructions comprising a laser light source having an optical fiber exiting therefrom, a means for coupling and rotating the optical fiber, a means for axially stepping the optical fiber and a catheter for receiving the optical fiber having a protective shield. The coupling and rotating means includes an optical rotary coupling device. The optical rotary coupling device rotates at 0 to 5000 rotations per minute. The axially stepping means includes a rotary axial stepper motor. The axial stepper motor moves the optical fiber axially at increments from between one micron and one millimeter.

The optical fiber may include a flat polished end face, an angle polished end face, an angle concave polished end face, a concave polished end face, a convex polished end face or an angle convex polished end face. The catheter includes a means for limiting oscillation of the optical fiber during rotation including a plurality of nubs located at the interior of the catheter. A computerized monitoring and guidance system for controlling and calculating the desired movements of the optical fiber is included which compares the data regarding the obstructing material with the desired movement.

The present invention relates to a method of ablating obstructing vascular or arterial material including the steps of inserting an optical fiber through a laser light source an optical rotary coupler, a rotary axial stepper motor and into a catheter, rotating the optical fiber at a predetermined rate, axially stepping the optical fiber at a predetermined increment, emitting laser light from the polished end face of the optical fiber and ablating obstructing material along a predetermined focal point pathway. An axial rotary stepper including a removable slug for interchanging variously polished optical fibers.

BRIEF DESCRIPTION OF THE DRAWINGS

FIG. 1 is a side elevation view of an embodiment of a tip of an optical fiber of the present invention having a flat polish;

FIG. 2 is a side elevation view of an alternate embodiment of a tip of an optical fiber of the present invention having an angle polish;

FIG. 3 is a side elevation view of an alternate embodiment of a tip of an optical fiber of the present invention having and angle concave polish;

FIG. 4 is a side elevation view of an alternate embodiment of a tip of an optical fiber of the present invention having an end concave polish;

FIG. 5 is a side elevation view of an alternate embodiment of a tip of an optical fiber of the present invention having an end convex polish;

FIG. 6 is a side elevation view of an alternate embodiment of a tip of an optical fiber of the present invention having an angle convex polish; and FIG. 7 is a schematic representation of the present invention.

DETAILED DESCRIPTION OF THE PRESENTLY PREFERRED EMBODIMENTS

The present invention relates to an optical fibre and laser apparatus for removal of arterial or vascular obstructions as best disclosed in FIG. 7. In a preferred embodiment a laser light source 10 is attached to an optical rotary coupling 20. The optical rotary coupling 20 is connected to a rotary axial stepper 30. An optical fibre 40 protrudes form the rotary axial stepper into a catheter 50. This arrangement of devices may be rearranged and other equivalent devices substituted to provide the method of removal of arterial or vascular obstructions of the present invention. The laser light source 10 is capable of adjusting the emitted wavelength in correspondence to the light absorption characteristics of the plaque or other obstructive material to be removed. For example, it is known that arterial plaque responds to light of wavelengths of 200 to 800 nanometers. A preferred embodiment includes a tunable laser (New Focus, Inc. Sunnyvale, Calif.). In a preferred embodiment the laser light source 10 is connected to optical fibre 40 which protrudes therefrom and passes through the optical rotary coupling 20. The optical fibre is received by an annulus 42 having a variable inner diameter. The annulus 42 has a standard outer diameter and is interchangeable to the optical rotary coupling 20. The annulus 42 is rotated by the optical rotary coupling 20 mechanism to rotate the optical fibre 40 at a predetermined rate. In a preferred embodiment the rotary optical coupler may rotate from 0 to 5,000 rotations per minute. The optical rotary coupler 20 may receive varying sized optical fibers having a range of diameters from 1 micron to 1000 microns.

The optical fibre 40 exits the optical rotary coupler 20 and enters a rotary axial stepper 30. The rotary axial stepper can control the movement of the optical fiber in the axial direction having step resolution of between 1 micron to 1 millimeter. The optical fibre 40 exits the rotary axial stepper 30 and is inserted in a catheter 50. In a preferred embodiment the catheter 50 has been pre-positioned within an artery or vein adjacent to the obstructed area. In a preferred embodiment the catheter includes a glass protective window 52 at its end/tip. Upon programming of a computerized monitoring and guidance system 60 attached to these apparatus with the proper rate of rotation, axial movement and wavelength dependent on the measurement and consistency of the obstructive material, the optical fiber is energized and while rotating is moved axially from point 54 to point 52 along the catheter 50. The movement of the optical fibre 40 will focus the laser light on the obstructing material and ablate the material and carve out a circular path of ablated material. The focusing of the laser light ablates the obstructing material by increasing the temperature of the obstructing material to its melting point. By careful selection of the proper wavelength and of the proper optical fibre 40 having the appropriate polished tip (see FIGS. 1–6) the melting point of the obstructing material can be reached at the focal point of the laser light. This focal point can be specifically controlled so that it falls only within the obstructing material and not the wall of the artery or vein. As well, it is known that arterial or vascular membranes have a higher melting point than most obstructing materials. In fact, it is known that most obstructing materials having a melting point slightly higher than normal body temperature and therefore only a slight amount of laser light, focused for a short amount of time is necessary to ablate the obstructing material.

The catheter 50 includes a plurality of channel nubs which protrude from the interior walls of the catheter 50 along its entire length. These hubs abut the sides of the optical fiber 40 and limit it from oscillating when the optical fiber 40 is rotating. Because the diameter of the interior of the catheter 50 is much larger than the diameter of the optical fiber 40 the rotation of the optical fiber at speeds of up to 5,000 rotations per minute could cause the optical fiber 40 to oscillate. Such oscillations would destroy the precision alignment of the focal point of the laser light path directed to the obstructing material. Thus, a means is provided for maintaining the centered orientation of the optical fiber 40 within the catheter 50. Hubs 53 have been provided in the preferred embodiment, however any means for inhibiting oscillation of the optical fiber 40 is anticipated by the present invention.

Turning to FIG. 1–6 it will become apparent that the present invention may be used with any combination of optical fibers having any type of polished end face. The type of polished end of the optical fibre which is inserted through the optical rotary coupler 20 to the rotary axial stepper 30 and into the catheter 50 can be interchangeable depending on the application. Certain polished end faces will be more effective for ablation of obstructing material depending on the placement, thickness and composition of the obstructing material. FIG. 1 shows an optical fibre 40 having a flat polished end face 41. Having an optical fibre with such a polish causes the path of the laser light 43 to disperse in a widening angular path away from the end 41 depending on the numerical aperture of the fiber selected. The flat polished end 41 causes laser light which does not have a focal point. Such a flat polished optical fibre could be used to ablate obstructing material which lies directly in front of the end face 41.

FIG. 2 shows an optical fibre 40 having an angle polish. Such an angle polish at the end face 41 causes a laser light path 48 which is broader than the laser light path 43 of the flat polished end face of FIG. 1. Such an angle polished end face may be used for ablation of obstructions that are parallel to the fiber probe.

FIG. 3 shows an optical fibre having an angle concave polished end face 41. Such a polish causes the laser light path 44 to cross at focal point 70. The focusing of the laser light at focal point 70 will cause the temperature at the focal point to be higher than any other point along the laser light path 44. Thus, the positioning of the focal point 70 of the angle concave polished optical fibre 40 will allow ablation at a specified point. Movement of the optical fibre 40 will move the focal point 70, causing the raising of the temperature of the obstructing material and ablation along a predetermined path. Thus, rotation and axial stepping of the optical fibre 40 along the catheter 50 will ablate the obstructing material of a vein or artery along the path of the focal point 70 of the laser light path 44. The fine control of the rotary axial stepper 30 in increments as small as 1 micron allow for control of the focal point to ablate virtually any obstructing material in any location. The rotary axial stepper controls the focal point 70 in the x axis; the optical rotary coupler 20 controls the focal point in the y axis and the polish of the end face 41 of the optical fibre 40 controls the focal point 70 in the z axis. The fine control of the location of the focal point 70 in three dimensions allows for the precision ablation without chance of harming the arterial or vascular wall. In a preferred embodiment the optical rotary coupler 20 may include a Picomotor (New Focus, Inc., Sunnyvale, Calif.); a linear and rotary actuator (BEI, Inc., San Marcos, Calif.); and a rotary joint (Focal Technologies, Dartmouth, Nova Scotia). In combination with the control of the wavelength of the laser light via the laser light source 10 the risk of damage to arterial or vascular walls is greatly reduced over prior ablation methods.

FIG. 4 shows an optical fibre 40 having an end face 41 with a concave polish. Such a polish causes the laser light to have a path which forms focal point 72. Such a concave polished optical fibre could be used for ablating a path in the obstructing material in an axial line corresponding to the movement of the axial stepper 30.

FIG. 5 shows an optical fibre 40 having a end face 41 with a flat convex polish. Such a polish causes a laser light path without a focal point. Such a polished optical fibre could be used for ablation of obstructions require a circular pattern that can be stepped forward or backward.

FIG. 6 shows an optical fibre 40 having an end face 41 with and angle convex polish. Such a polish causes a laser light path 49 which does not have a focal point. Such a polished optical fibre 40 could be used for wide angle ablation of obstructions that are parallel to the fiber probe. Other polished end faces are anticipated by the present invention and the use of such variably polished optical fibers interchangeably in any combination is also envisioned herein.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

What is claimed is:

1. An optical fiber and laser apparatus for removal of arterial and vascular obstructions, said apparatus comprising:

(a) a laser light source capable of generating a laser light for the ablation of an arterial or vascular obstruction;
   (b) a rotatable optical fiber exiting from said laser light source;
   (c) means for rotating said optical fiber;
   (d) means for longitudinally stepping said optical fiber, said means for longitudinally stepping including a longitudinal stepper motor; and
   (e) a catheter for receiving said optical fiber, said catheter having a protective shield, wherein said optical fiber directs said laser light from said laser light source to an arterial or vascular obstruction while rotating or longitudinally stepping or simultaneously rotating and longitudinally stepping said optical fiber.

2. The apparatus of claim 1, wherein said means for rotating said optical fiber includes an optical rotary device.

3. The apparatus of claim 2, wherein said optical rotary device rotates at 0 to 5000 rotations per minute.

4. The apparatus of claim 2 wherein said optical rotary device includes a removable annulus for interchanging variously polished optical fibers.

5. The apparatus of claim 1, wherein said longitudinal stepper motor advances or retracts said optical fiber longitudinally at increments from between 1 micron and 1 millimeter.

6. The apparatus of claim 1 wherein said optical fiber includes a flat polished end face.

7. The apparatus of claim 1 wherein said optical fiber includes an angle polished end face.

8. The apparatus of claim 1 wherein said optical fiber includes an angle concave polished end face.

9. The apparatus of claim 1 wherein said optical fiber includes a concave polished end face.

10. The apparatus of claim 1 wherein said optical fiber includes a convex polished end face.

11. The apparatus of claim 1 wherein said optical fiber includes an angle convex polished end face.

12. The apparatus of claim 1 wherein said catheter includes a means for limiting oscillation of said optical fiber during rotation.

13. The apparatus of claim 12 wherein said means for limiting oscillation includes a plurality of nubs located at the interior of said catheter.

14. The apparatus of claim 1, further including a computerized monitoring and guidance system connected to the means for rotating and to the means for longitudinally stepping, said computerized monitoring and guidance system controlling and calculating desired movements of said optical fiber in response to data regarding the obstruction.

15. A method of ablating obstructing vascular or arterial material, said method comprising the steps of:

(a) inserting an optical fiber and laser apparatus into an arterial or vascular structure, said apparatus comprising (i) a laser light source capable of generating a laser light for the ablation of an arterial or vascular obstruction, (ii) a rotatable optical fiber exiting from said laser light source, (iii) means for rotating said optical fiber, (iv) means for longitudinally stepping said optical fiber including a longitudinal stepping motor; and (v) a catheter for receiving said optical fiber;
   (b) rotating said optical fiber at a predetermined rate or longitudinally stepping said optical fiber using a longitudinal stepping motor at a predetermined increment or simultaneously rotating said optical fiber at a predetermined rate and longitudinally stepping said optical fiber at a predetermined increment; and
   (c) generating a laser light through said optical fiber with said laser light source while rotating or longitudinally stepping or simultaneously rotating and longitudinally stepping said optical fiber, whereby said optical fiber directs said laser light to an arterial or vascular obstruction for the ablation thereof.

* * * * *